United States Patent [19]

Frost et al.

[11] Patent Number: 5,272,073
[45] Date of Patent: Dec. 21, 1993

[54] BIOCATALYTIC SYNTHESIS OF CATECHOL FROM GLUCOSE

[75] Inventors: John W. Frost, Lafayette, Ind.; Karen M. Draths, Pasadena, Calif.

[73] Assignee: Purdue Research Foundation, West Lafayette, Ind.

[21] Appl. No.: 906,976

[22] Filed: Jun. 30, 1992

[51] Int. Cl.⁵ .................. C12P 7/02; C12P 7/22; C12N 15/70; C12N 15/74
[52] U.S. Cl. .................. 435/155; 435/156; 435/252.3; 435/252.33; 435/320.1; 435/849; 435/852; 536/23.2; 935/29; 935/60; 935/68; 935/72; 935/73
[58] Field of Search ............ 435/155, 156, 320.1, 435/849, 852, 252.3, 252.33, ; 536/27, 23.2

[56] References Cited

U.S. PATENT DOCUMENTS 4,863,861  9/1989  Schofield ............ 435/155
5,168,056  12/1992  Frost ............ 435/172.3

OTHER PUBLICATIONS

Draths, K. M., and Frost, J. W., 1990, Journal of the American Chemical Society, 112(23):9630–9632.
Frost, J. W. et al., 1984, Biochemistry 23(19):4470–4475.
Millar, G. and Coggins, J. R., 1986, FEBS Letters 200(1):11–17.
Bruce, N. C., and Cain, R. B., 1990, Archives of Microbiology 154(1):179–186.
Brewster, D., et al., 1976, Biochemical Society Transactions, 4:518–521.
Brewster, D. et al., 1978, Biochemical Journal 170:257–264.
Cánovas, J. L. et al., 1968, European Journal of Biochemistry, 3:293–504.
Ingledew, W. M., et al., 1971, Journal of General Microbiology, 68(1):273–282.
Tresguerres, M. E. F., et al., 1972, Archiv Für Mikrobiologie, 82:111–119.
Lamb, H. K., et al., 1991, Molecular and General Genetics, 227:187–196.
Cain, R. B., 1969, Biochemical Journal, 114(4):76P.
Chaleff, R. S., 1974, Journal of General Microbiology 81:337–355.
Shirai, K., Agric. Biol. Chem., 1987, 51(1), 121–128.
Shirai, K., Agric. Biol. Chem., 1986, 50(11), 2875–2880.
Nei, N. et al., J. Ferment, Technol., 1974, vol. 52, No. 1, 28–34.
Nishimura, T. et al., Yaki Gosei Kagaku Kyokai Shi, 1976, 34, 652–656.
Tatum, E. L. et al., Proced. Nat. Acad. Sci. (1954), vol. 40, pp. 271–276.
Scharf, K. H. et al., Chem. Comm. (1971), pp. 765–766.
Tatum, E. L. et al., J. Biol. Chem. (1956), vol. 219, pp. 797–807.
Pittard, A. J. et al., Biochim. et Biophys. Acta (1962), vol. 57, pp. 290–298.
White, A. et al., "Principles of Biochemistry", 6th edition, McGraw-Hill Book Co., New York, 1978.
Frost, J. W. et al., Journ. Am. Chem. Soc. (1991), 113(24), pp. 9361–9363.
Zubay, G.; "Biochemistry", Addison-Wesley Publishing Co., Reading, Mass., 1983.

Primary Examiner—Robert A. Wax
Assistant Examiner—William W. Moore
Attorney, Agent, or Firm—Margaret A. Horn

[57] ABSTRACT

There is described a biocatalytic method for the synthesis of cathecol from a renewable source such as glucose. The method comprises inducing a divergent pathway in the shikimate pathway of a host cell. Additionally, there are described methods for making precursors to cathecol such as protocatechuate.

10 Claims, 1 Drawing Sheet

BIOCATALYTIC SYNTHESIS OF CATECHOL FROM GLUCOSE

BACKGROUND OF THE INVENTION

This invention relates to the production of catechol and precursors thereof by the conversion of D-glucose. This invention has been described by the inventors hereto, Frost and Draths, in the *J of Am. Chem. Soc* 1991, 113, No 24, which reference is incorporated herein in its entirety. Catechol is an exceptionally important molecule used as a starting material in the synthesis of pharmaceuticals, pesticides, flavors, fragrances, and polymerization inhibitors.

Production of catechol is currently based on hydroxylation of phenol or distillation of coal-tar. Forceful alkaline hydrolysis of o-chlorophenol was used in the recent past to produce catechol. Fries peroxide rearrangement of salicylaldehyde, cleavage of the monomethyl ether of guaiacol, and biocatalytic oxidation of benzene, benzoate, or phenol are alternative routes which can lead to catechol.

These previous routes of biocatalytic production of catechol require the use of environmentally undesirable compounds such as phenol, benzoic acid or benzene as starting materials, all of which are derived from nonrenewable fossil fuels. Furthermore, previous chemical synthesis of catechol require high temperatures, caustic solutions, metals and peroxides, all of which are viewed as undesirable from an industrial and environmental perspective.

Thus it would be beneficial to develop a method for production of catechol and its precursors starting with a renewable resource, which method would not require caustic agents, metals or other environmentally undesirable agents.

Therefore, it is the intent of the present invention to provide a method for the production of catechol, which method utilizes D-glucose as a starting material, which starting material is derived from a renewable resource such as corn, sugar beets or sugar cane.

SUMMARY OF THE INVENTION

This invention relates to a method for the production of catechol, precursors or derivatives thereof, from the common aromatic pathway of a host cell (such as shown in FIG. 1) starting from D-glucose the method comprising inducing expression of a divergent pathway in such host cell. More specifically such divergent pathway consists of DHS dehydratase and protocatechuate decarboxylase.

In an embodiment of the present invention the divergent pathway is induced by transforming the host cell with recombinant DNA comprising a gene coding for transketolase (tkt), a gene coding for an isozyme of DAHP synthase (aroF) and a gene coding for 3-dehydroquinate synthase (aroB). Plasmid pKD136 carries tkt, aroF and aroB which encode the enzymes transketolase, the tyrosine-sensitive isozyme of DAHP synthase, and 3-dehydroquinate synthase, respectively. The construction of pKD136 and expression of pKD136 by *E. coli* aroE has previously been described. (See Draths, K. M.; Frost, J. W. *J. Am. Chem. Soc.*, 1990, 112, 9630. Plasmid pkD136 was constructed by inserting the aroB gene in plasmid pkD130A. Plasmid pkD130A is described in Draths, K. M.; Frost. J. W. *J. Am. Chem. Soc.* 1990, 112. 1657. A 1.65 kb fragment containing the aroB locus (as described in Frost, J. W.; Bender, J. L.; Kadonaga, J. T.; Knowles, J. R. *Biochemistry* 1984, 23, 4470 and Millar, G.; Coggins, J. R. *FEBS Lett.* 1986, 200, 11) was introduced into the SphI site of plasmid pkD130A to produce pkD136. Genetic manipulations were carried out following procedures described by Maniatis, T.; Fritsch, E. F.; Sambrook, J. *Molecular Cloning: A Laboratory Manual*; Cold Spring Harbor Laboratory; Cold Spring Harbor, 1982. Plasmid pkD136 was transformed into *E. coli AB* 2834aroE.

In a preferred embodiment of the present invention, the host cell is *Escherichia coli*, and particularly *E. coli* strain aroA/pKD136 or strain aroC/pKD136.

DETAILED DESCRIPTION OF THE INVENTION

Figure 1:
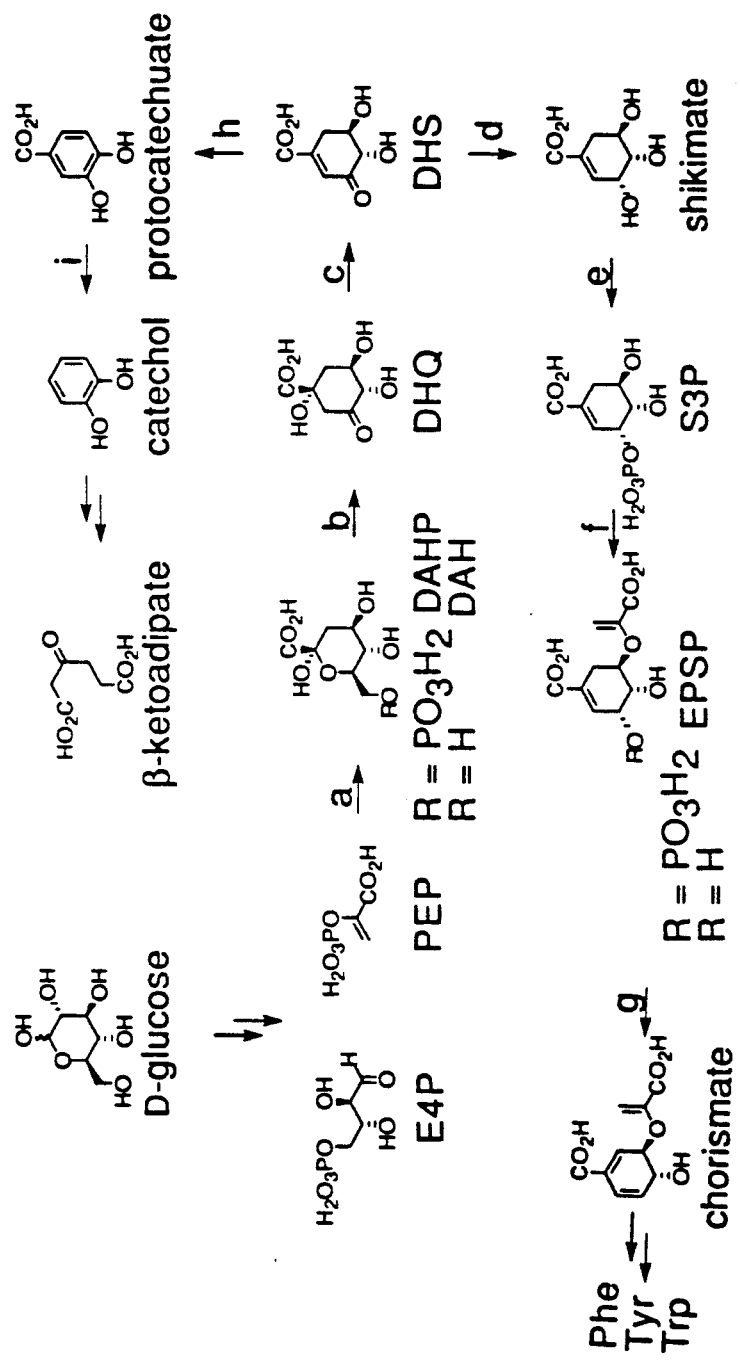
FIG. 1 is a schematic of a common pathway of aromatic biosynthesis (enzymes a-g) and the divergent pathway of the present invention (enzymes h and i).

Common aromatic pathways starting from D-glucose are known for various microorganisms for the production of various aromatic compounds. The common aromatic pathway (FIG. 1) useful in the present invention starts from D-glucose and ultimately leads to chorismate with many intermediates or precursor compounds in the pathway. The enzymes comprised in such pathway include DAHP synthase (aroF), DHQ synthase (aroB), DHQ dehydratase (aroD), shikimate dehydrogenase (aroE), shikimate kinase (aroL), EPSP synthase (aroA) and chorismate synthase (aroC). This common pathway is represented in FIG. 1 as enzymes a-g. It has been found that host cells can be induced to form a divergent pathway from this common pathway whereby catechol and protocatechuate are formed by the expression of a pathway consisting of DHS dehydratase and protocatechuate decarboxylase. This divergent pathway is shown in FIG. 1 as enzymes h and i.

Enhanced expression of genes coding from proteins able to perform or control the induction of this divergent pathway or common aromatic pathway enzymatic functions is mediated by genetic elements transferable into a host cell. Genetic elements as herein defined include nucleic acids (generally DNA or RNA) having expressible coding sequences for products such as proteins, apoproteins, or antisense RNA, which can perform or control pathway enzymatic functions. The expressed proteins can function as enzymes, repress or derepress enzyme activity, or control expression of enzymes. The nucleic acids coding these expressible sequences can be either chromosomal (e.g. integrated into a host cell chromosome by homologous recombination) or extrachromosomal (e.g. carried by plasmids, cosmids, etc). In addition, genetic elements are defined to include optional expression control sequences including promoters, repressors, and enhancers that act to control expression or derepression of coding sequences for proteins, apoproteins, or antisense RNA. For example, such control sequences can be inserted into wild type host cells to promote over expression of selected enzymes already encoded in the host cell genome, or alternatively can be used to control synthesis of extrachromosomally encoded enzymes.

The genetic elements of the present invention can be introduced into a host cell by plasmids, cosmids, phages, yeast artificial chromosomes or other vectors that mediate transfer of the genetic elements into a host cell. These vectors can include an origin of replication along with cisacting control elements that control replication of the vector and the genetic elements carried by the vector. Selectable markers can be present on the vector to aid in the identification of host cells into which the genetic elements have been introduced. For example, selectable markers can be genes that confer resistance to particular antibiotics such as tetracycline, ampicillin, chloramphenicol, kanamycin, or neomycin.

A preferred means for introducing genetic elements into a host cell utilizes an extrachromosomal multi-copy plasmid vector into which genetic elements in accordance with the present invention are inserted. Plasmid borne introduction of the genetic element into host cells involves an initial cleaving of a plasmid with a restriction enzyme, followed by ligation of the plasmid and genetic elements in accordance with the invention. Upon recircularization of the ligated recombinant plasmid, transduction or other mechanism for plasmid transfer is utilized to transfer the plasmid into the host cell. Plasmids suitable for insertion of genetic elements into the host cell include but are not limited to PKD136.

Suitable host cells for use in the present invention are members of those genera capable of being utilized for industrial biosynthetic production of desired aromatic compounds. Accordingly, host cells can include microbes belonging to a genera possessing DHS dehydratase and/or protocatechuate decarboxylase, including but not limited to Escherichia or Klebsiella.

For industrial production of catechol and other metabolites derived from the divergent pathway stemming from the chorismate pathway, deregulated mutant strains of the above recited genera that lack feedback inhibition of one or more enzymes in the metabolic biosynthetic pathway are preferred. Such strains can be created by random or directed mutagenesis, or are commercially available. See for example U.S. Pat. No. 4,681,852 or U.S. Pat. No. 4,753,883.

In a preferred embodiment of the present invention, catechol is synthesized by *E. coli*. This synthesis by *E. coli* has led to the discovery of a pathway which can siphon away most of the D-glucose equivalents initially directed into the common pathway of aromatic biosynthesis (See FIG. 1). Induction of the discovered pathway constitutes an important variable to consider in the design of biocatalytic syntheses of aromatic amino acids and related secondary metabolites. The induced pathway may also be a useful route for converting D-glucose into catechol, a molecule from which a variety of pharmaceuticals, pesticides, flavors, and polymerization inhibitors are industrially derived.

As has been previously described in the literature, the percentage of D-glucose consumed by *E. coli* which is siphoned into aromatic biosynthesis is greatly increased when transketolase (tkt) and an isozyme of DAHP synthase (aroF) are amplified upon transformation with plasmid pKD136. Draths, K. M; Frost, J. W. *J. Am. Chem. Soc.* 1990, 112, 1657. In addition to tkt and aroF, pKD136 carries an aroB locus which prevents accumulation of 3-deoxy-D-arabino-heptulosonic acid (DAH). Expression of pKD136 by *E. coli* aroE results in synthesis of a 30 mM concentration of 3-dehydroshikimate. Draths, K. M; Frost, J. W. *J. Am. Chem. Soc.* 1990, 112, 9630. In contrast, it has been found that *E. coli* aroA/pKD136 accumulates only 2.4 mM shikimate 3-phosphate in its culture supernatant and *E. coli* aroC/pKD136 synthesizes a 3.8 mM concentration of 5-enolpyruylshikimate (EPS). Thus, on the basis of concentrations of metabolites accumulated by aroE, aroA, and aroC mutants of *E. coli*, approximately 90% of the D-glucose equivalents directed into aromatic biosynthesis are lost after DHS formation.

It has surprisingly been found that the loss of approximately 90% of the glucose equivalents are to a large extent related to the induction of the divergent pathway consisting of DHS dehydratase and protocatechuate decarboxylase resulting in accumulation of catechol. These enzymes have not previously been detected in *E. coli*. Furthermore, a drastic increase in the number of D-glucose equivalents directed into aromatic biosynthesis is not precedented to induce DHS dehydratase or protocatechuate decarboxylase in microbes known to possess these enzymes. Tatum et al *J. Biol Chem* 1956, 219,797; Pittard et al *Biochim. Biophys Acta* 1962, 57, 290.

Experimental

Conversion of D-Glucose into Catechol

The highest concentrations of catechol (3.75 mM) were produced by *E. coli* AB2829 aroA/pKD136 and *E. coli* AB2849 aroC/pKD136. Culturing conditions, $^1$H NMR analysis, and catechol isolation is presented for *E. coli* AB2829 aroA/pKD136. An overnight culture of this strain was used to inoculate (0.5% inoculant) 1 L of ampicillin-containing LB medium in a 4 L Erlenmeyer flask. Cells were cultured at 37° C. with agitation (200 rpm) for 8 h. After harvesting the cells (5000 g, 5 min. 4° C.), the supernatant was discarded and the cells were resuspended in 1 L (4 L Erlenmeyer flask) of M9 medium containing glucose (10 g) and ampicillin. The cells were returned to 37° C. incubation and agitation (200 rpm).

At timed intervals, a portion (25 mL) of the culture was removed and the cells were pelleted by centrifugation (15000 g, 10 min, 4°). After removal of the water in vacuo and exchange of residual water with $D_2O$, $^1$H NMR was used to analyze the molecules accumulating in the supernatant. The $^1$H NMR of the culture supernatant of *E. coli* AB2829 aroA/pKD136 36 h after resuspension in M9 medium is dominated by the resonances associated with catechol ($\delta$6.80 –7.00). Resonances associated with shikimate-3-phosphate are also observable.

Isolation of catechol from the culture supernatant of *E. coli* AB2829 aroA/pKD136 began with removal of cells from the M9 medium by centrifugation (15000 g, 10 min, 4° C.). The resulting supernatant was adjusted to pH 2.5 with 6 N HCl and then extracted six times with 500 mL portions of ethyl acetate. The organic fractions were combined, dried over magnesium sulfate, and concentrated to dryness. Radial chromatography (2 mm thickness of silica gel 60 $PF_{254}$ developed with 95:5; v/v, ethyl acetate: hexane) resulted in the isolation of catechol: $^1$H NMR ($D_2O$) $\delta$6.80–7.00 (m, 4H); $^{13}$C NMR ($D_2O$)$\delta$119.6, 124.4, 147.3; CIMS: 111 (M+H+).

DHS Dehydratase and Protocatechuate Decarboxylase Activities

*E. coli* AB2834 aroE/pKD136 was cultured in a manner similar to that described for *E. coli* AB2829 aroA/pKD136. After resuspension in M9 medium, *E. coli* AB2834 aroE/pKD136 cells were harvested when 3,4-dihydroxybenzoic acid was detected in the culture supernatant. The cells were disrupted, and particulate debris was removed by centrifugation. Cell lysate was incubated with DHS at 37° C. in a nitrogen atmosphere for 4 hours. The reaction was then acidified and extracted several times with ethyl acetate. The organic fractions were combined, concentrated to dryness, and concentrated several times with D$_2$O. Analysis of the extracted products by $^1$H NMR indicated that a large fraction of DHS had been converted into a mixture of catechol and 3,4-dihydroxybenzoic acid as indicated, respectively, by a resonance at δ6.80–7.00 (m, 4 H) and resonances at δ6.94 (d, 7 Hz, 1 H) and 7.48 (d, 7 Hz, 2H). Observation of protocatechuic acid and catechol is indicative of DHS dehydratase and protocatechuate decarboxylase activities, respectively. To verify that conversion of DHS into 3,4-dihydroxybenzoic acid was a result of DHS dehydratase activity and not due to the acidic reaction workup, DHS was treated similarly in the absence of cell lysate. $^1$H NMR indicated that less than 2% of the DHS aromatized to 3,4-dihydroxybenzoic acid. No catechol was detected in the absence of cell lysate. Similarly, DHS dehydratase activity was detected in *E. coli* AB2829 aroA/pKD136 and *E. coli* AB2849 aroC/pKD136 cell lysates

What is claimed is:

1. A method for the production of catechol or precursors thereof, from the shikimate common aromatic pathway of a host cell selected from the group consisting of the genera Escherichia and Klebsiella the method comprising:
    a) inducing a divergent pathway in the shikimate pathway by transforming the host cell with recombinant DNA comprising a gene coding for transketolase, a gene coding for an isozyme of DAHP synthase, and a gene coding for 3-dehydroquinate synthase; and
    b) culturing the transformants of step a) in glucose containing medium.

2. A method of claim 1 wherein the genes are tkt, aroF, and aroB.

3. A method of claim 1 wherein the divergent pathway comprises DHS dehydratase and protocatechuate decarboxylase.

4. A method of claim 1 wherein the transformed host cell expresses protocatechuate derived from dehydroshikimate.

5. A method of claim 4 wherein the dehydroshikimate is converted to protocatechuate by the enzymatic activity of DHS dehydratase.

6. A method of claim 1 wherein the transformed host cell expresses catechol derived from protocatechuate.

7. A method of claim 6 wherein the protocatechuate is converted to catechol by the enzymatic activity of protocatechuate decarboxylase.

8. A method of claim 1 further comprising converting the catechol to β-ketoadipate.

9. A method of claim 1 wherein the host cell is aroA/pKD136.

10. A method of claim 1 wherein the host cell is aroC/pKD136.

* * * * *